United States Patent [19]

Khrapko et al.

[11] Patent Number: 5,552,270
[45] Date of Patent: Sep. 3, 1996

[54] METHODS OF DNA SEQUENCING BY HYBRIDIZATION BASED ON OPTIMIZING CONCENTRATION OF MATRIX-BOUND OLIGONUCLEOTIDE AND DEVICE FOR CARRYING OUT SAME

[75] Inventors: Konstantin R. Khrapko; Alexandr A. Khorlin, both of Moscow; Igor B. Ivanov, Moskovskaya; Gennady M. Ershov, Moscow; Jury P. Lysov, Moscow; Vladimir L. Florentiev, Moscow; Andrei D. Mirzabekov, Moscow, all of Russian Federation

[73] Assignee: Institut Molekulyarnoi Biologii Imeni V.A., Moscow, Russian Federation

[21] Appl. No.: 949,541

[22] PCT Filed: Mar. 18, 1992

[86] PCT No.: PCT/RU92/00052

§ 371 Date: Nov. 9, 1992

§ 102(e) Date: Nov. 9, 1992

[87] PCT Pub. No.: WO92/16655

PCT Pub. Date: Oct. 1, 1992

[30] Foreign Application Priority Data

Mar. 18, 1991 [SU] U.S.S.R. ................... 4919321

[51] Int. Cl.[6] .................. C12Q 1/68; G01N 33/48
[52] U.S. Cl. .................. 435/6; 436/94; 436/501; 422/55; 422/56; 422/57; 422/58; 422/68.1
[58] Field of Search .................. 422/55, 56, 57, 422/58, 68.1; 436/94, 501; 935/77, 78; 435/6

[56] References Cited

U.S. PATENT DOCUMENTS 5,002,867 3/1991 Macevicz ..................... 435/6
5,202,231 4/1993 Drmanac et al. .............. 435/6

FOREIGN PATENT DOCUMENTS

| 0132621 | 2/1985 | European Pat. Off. . |
| 0159719 | 10/1985 | European Pat. Off. . |
| 0266787 | 5/1988 | European Pat. Off. . |
| 0322311 | 6/1989 | European Pat. Off. . |
| 89-10977 | 11/1989 | WIPO . |

OTHER PUBLICATIONS

Khrapko et al., *DNA Sequence—J. DNA Sequ. Mapp.* 1(6), 375–388 (30 Jul. 1991).
Lysov et al., *Doklady Akad Nauk SSSR* 303(6), 1508–1511 (1988).
Khrapko et al. *FEBS Lett.* 256(1,2), 118–122 (1989).
Bains et al., *J. Theor. Biol.* 135, 303–307 (1988).
Strezoska et al., *PNAS* 88, 10089–10093 (1991 Nov.).
Pevzner, *J. Biomolec. Struc. Dyn.* 7(1), 63–69 (1989).
Pevzner et al., *J. Biomolec. Struc. Dyn.* 9(2), 399–410 (1991).
Southern et al., *Genomics* 13, 1008–1017 (1992).
Cotton, Richard G H; "Detection of single base changes in nucleic acid", The Biochemical Journal, vol. 263, No. 1 (Oct. 1, 1989), pp. 1–10.
Nucleic Acids Research, vol. 6, No. 11 (Aug. 10, 1979), pp. 3442–3444, 3446–3458.
Ivanov, I. B. et al. Nucleic Acids Research Symposium Ser. No. 24 (1991) p. 189–190.
Livshits, M. A. Journal of Biomolecular Structure & Dynamics vol. 11(4) 1994 pp. 783–795.

*Primary Examiner*—Kenneth R. Horlick
*Attorney, Agent, or Firm*—Ladas & Parry

[57] ABSTRACT

A method for sequencing DNA by hybridization that includes the following steps: forming an array of oligonucleotides at such concentrations that either ensure the same dissociation temperature for all fully complementary duplexes or allows hybridization and washing of such duplexes to be conducted at the same temperature; hybridizing said oligonucleotide array with labeled test DNA; washing in duplex dissociation conditions; identifying single-base substitutions in the test DNA by analyzing the distribution of the dissociation temperatures and reconstructing the DNA nucleotide sequence based on the above analysis. A device for carrying out the method comprises a solid substrate and a matrix rigidly bound to the substrate. The matrix contains the oligonucleotide array and consists of a multiplicity of gel portions. Each gel portion contains one oligonucleotide of desired length. The gel portions are separated from one another by interstices and have a thickness not exceeding 30 µm.

9 Claims, 7 Drawing Sheets

SEQUENCE LISTING ( 1 ) GENERAL INFORMATION:

( i i i ) NUMBER OF SEQUENCES: 47

( 2 ) INFORMATION FOR SEQ ID NO:1:

( i ) SEQUENCE CHARACTERISTICS:
        ( A ) LENGTH: 17 bases
        ( B ) TYPE: nucleic acid
        ( C ) STRANDEDNESS: single (D) TOPOLOGY: Linear (ii) MOLECULE TYPE: chemically synthesized
desoxyribooligonucleotide (ix) FEATURE: oligonucleotide was synthesized by phosphoroamidite
method
(D) OTHER INFORMATION: The "d"before the sequence represents
that the sequence is desoxyribonucleic acid (DNA rather
than RNA).

(xi) SEQUENCE DESCRIPTION: SEQ ID NO:1:

GTAAAACGAC GGCCAGT 17

(2) INFORMATION FOR SEQ ID NO:2:

(i) SEQUENCE CHARACTERISTICS:
(A) LENGTH: 17 bases
(B) TYPE: nucleic acid
(C) STRANDEDNESS: single
(D) TOPOLOGY: Linear (ii) MOLECULE TYPE: chemically synthesized
desoxyribooligonucleotide (ix) FEATURE: oligonucleotide was synthesized by phosphoroamidite
method.
(D) OTHER INFORMATION: The "d"before the sequence represents
that the sequence is desoxyribonucleic acid (DNA rather
than RNA).

(i) SEQUENCE DESCRIPTION: SEQ ID NO:2:

GTAAAACGAT GGCCAGT 17

(2) INFORMATION FOR SEQ ID NO:3:

(i) SEQUENCE CHARACTERISTICS:
(A) LENGTH: 17 bases
(B) TYPE: nucleic acid
(C) STRANDEDNESS: single
(D) TOPOLOGY: Linear (ii) MOLECULE TYPE: chemically synthesized
desoxyribooligonucleotide (ix) FEATURE: oligonucleotide was synthesized by phosphoroamidite
method
(D) OTHER INFORMATION: The "d"before the sequence represents
that the sequence is desoxyribonucleic acid (DNA rather
than RNA).

(xi) SEQUENCE DESCRIPTION: SEQ ID NO:3:

GTAAAACGAA GGCCAGT 17

(2) INFORMATION FOR SEQ ID NO:4:

(i) SEQUENCE CHARACTERISTICS:
(A) LENGTH: 17 bases
(B) TYPE: nucleic acid
(C) STRANDEDNESS: single
(D) TOPOLOGY: Linear (ii) MOLECULE TYPE: chemically synthesized
desoxyribooligonucleotide.

(ix) FEATURE: oligonucleotide was synthesized by phosphoroamidite
method.
(D) OTHER INFORMATION: The "d"before the sequence represents
that the sequence is desoxyribonucleic acid (DNA rather
than RNA).

(i) SEQUENCE DESCRIPTION: SEQ ID NO:4:

GTAAAACGAC CGCCAGT 17

( 2 ) INFORMATION FOR SEQ ID NO:5:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
        method
        ( D ) OTHER INFORMATION: letter M means the tethering to the
        support via oxidized 3-methyluridine.

( x i ) SEQUENCE DESCRIPTION: SEQ ID NO:5:

G T C G T T T T    8

( 2 ) INFORMATION FOR SEQ ID NO:6:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method
        ( D ) OTHER INFORMATION: The sequence is listed from 3' to 5'
        left to right and this is a part of SEQ ID NO:1.

( x i ) SEQUENCE DESCRIPTION: SEQ ID NO:6:

G C A G C A A A A T    1 0

( 2 ) INFORMATION FOR SEQ ID NO:7:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
        method.
        ( D ) OTHER INFORMATION: The sequence is listed from 3' to 5'
        left to right and this is part of SEQ ID NO:2.

( x i ) SEQUENCE DESCRIPTION: SEQ ID NO:7:

G T A G C A A A A T    1 0

( 2 ) INFORMATION FOR SEQ ID NO:8:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoromidite
        method.
        ( D ) OTHER INFORMATION: The sequence is listed from 3' to 5'
        left to right and this is a part of SEQ ID NO:3.

( x i ) SEQUENCE DESCRIPTION: SEQ ID NO:8:

GAAGCAAAAT          10

( 2 ) INFORMATION FOR SEQ ID NO:9:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
        method
        ( D ) OTHER INFORMATION: letter M means the tethering to the
        support via oxidized 3-methyluridine.

( x i ) SEQUENCE DESCRIPTION: SEQ ID NO:9:

CGTCGTTT          8

( 2 ) INFORMATION FOR SEQ ID NO:10:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
        method.
        ( D ) OTHER INFORMATION: The sequence is listed from 3' to 5'
        left to right and this is a part of SEQ ID NO:1.

( x i ) SEQUENCE DESCRIPTION: SEQ ID NO:10:

GGCAGCAAAA          10

( 2 ) INFORMATION FOR SEQ ID NO:11:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3' to 5'
        left to right and this is a part of SEQ ID NO:2.

( x i ) SEQUENCE DESCRIPTION: SEQ ID NO:11:

GGTAGCAAAA          10

( 2 ) INFORMATION FOR SEQ ID NO:12:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
method.
( D ) OTHER INFORMATION: The sequence is listed from 3' to 5'
left to right and this is a part of SEQ ID NO:3.

( x i ) SEQUENCE DESCRIPTION: SEQ ID NO:12:

G G A A G C A A A A    1 0

( 2 ) INFORMATION FOR SEQ ID NO:13:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
method.
        ( D ) OTHER INFORMATION: The sequence is listed from 3' to 5'
left to right and this is a part of SEQ ID NO:4.

( x i ) SEQUENCE DESCRIPTION: SEQ ID NO:13:

G C C A G C A A A A    1 0

( 2 ) INFORMATION FOR SEQ ID NO:14:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
method
        ( D ) OTHER INFORMATION: letter M means the tethering to the
support via oxidized 3-methyluridine.

( x i ) SEQUENCE DESCRIPTION: SEQ ID NO:14:

C C G T C G T T    8

( 2 ) INFORMATION FOR SEQ ID NO:15:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
method.
        ( D ) OTHER INFORMATION: The sequence is listed from 3' to 5'
left to right and this is a part of SEQ ID NO:1.

( x i ) SEQUENCE DESCRIPTION: SEQ ID NO:15:

C G G C A G C A A A    1 0

( 2 ) INFORMATION FOR SEQ ID NO:16:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
desoxyribooligonucleotide ( i x ) FEATURE: oligonucleotide was synthesized by phosphoroamidite
method.
( D ) OTHER INFORMATION: The sequence is listed from 3' to 5'
left to right and this is a part of SEQ ID NO:2.

( x i ) SEQUENCE DESCRIPTION: SEQ ID NO:16:

CGGTAGCAAA  10

( 2 ) INFORMATION FOR SEQ ID NO:17:

( i ) SEQUENCE CHARACTERISTICS:
( A ) LENGTH: 10 bases
( B ) TYPE: nucleic acid
( C ) STRANDEDNESS: single
( D ) TOPOLOGY: Linear ( i i ) MOLECULE TYPE: chemically synthesized
desoxyribooligonucleotide ( i x ) FEATURE: oligonucleotide was synthesized by phosphoroamidite
method.
( D ) OTHER INFORMATION: The sequence is listed from 3' to 5'
left to right and this is a part of SEQ ID NO:3.

( x i ) SEQUENCE DESCRIPTION: SEQ ID NO:17:

CGGAAGCAAA  10

( 2 ) INFORMATION FOR SEQ ID NO:18:

( i ) SEQUENCE CHARACTERISTICS:
( A ) LENGTH: 10 bases
( B ) TYPE: nucleic acid
( C ) STRANDEDNESS: single
( D ) TOPOLOGY: Linear ( i i ) MOLECULE TYPE: chemically synthesized
desoxyribooligonucleotide.

( i x ) FEATURE: oligonucleotide was synthesized by phosphoroamidite
method.
( D ) OTHER INFORMATION: The sequence is listed from 3' to 5'
left to right and this is a part of SEQ ID NO:4.

( x i ) SEQUENCE DESCRIPTION: SEQ ID NO:18:

CGCCAGCAAA  10

( 2 ) INFORMATION FOR SEQ ID NO:19:

( i ) SEQUENCE CHARACTERISTICS:
( A ) LENGTH: 8 bases
( B ) TYPE: nucleic acid
( C ) STRANDEDNESS: single
( D ) TOPOLOGY: Linear ( i i ) MOLECULE TYPE: chemically synthesized
desoxyribooligonucleotide.

( i x ) FEATURE: oligonucleotide was synthesized by phosphoroamidite
method.
( D ) OTHER INFORMATION: letter M means the tethering to the
support via oxidized 3-methyluridine.

( x i ) SEQUENCE DESCRIPTION: SEQ ID NO:19:

GCCGTCGT  8

( 2 ) INFORMATION FOR SEQ ID NO:20:

( i ) SEQUENCE CHARACTERISTICS:

(A) LENGTH: 10 bases
(B) TYPE: nucleic acid
(C) STRANDEDNESS: single
(D) TOPOLOGY: Linear (i i) MOLECULE TYPE: chemically synthesized
desoxyribooligonucleotide.

(i x) FEATURE: oligonucleotide was synthesized by phosphoroamidite
method.
(D) OTHER INFORMATION: The sequence is listed from 3' to 5'
left to right and this is a part of SEQ ID NO:1.

(x i) SEQUENCE DESCRIPTION: SEQ ID NO:20:

CCGGCAGCAA 10

(2) INFORMATION FOR SEQ ID NO:21:

(i) SEQUENCE CHARACTERISTICS:
(A) LENGTH: 10 bases
(B) TYPE: nucleic acid
(C) STRANDEDNESS: single
(D) TOPOLOGY: Linear (i i) MOLECULE TYPE: chemically synthesized
desoxyribooligonucleotide.

(i x) FEATURE: oligonucleotide was synthesized by phosphoroamidite
method.
(D) OTHER INFORMATION: The sequence is listed from 3' to 5'
left to right and this is a part of SEQ ID NO:2.

(x i) SEQUENCE DESCRIPTION: SEQ ID NO:21:

CCGGTAGCAA 10

(2) INFORMATION FOR SEQ ID NO:22:

(i) SEQUENCE CHARACTERISTICS:
(A) LENGTH: 10 bases
(B) TYPE: nucleic acid
(C) STRANDEDNESS: single
(D) TOPOLOGY: Linear (i i) MOLECULE TYPE: chemically synthesized
desoxyribooligonucleotide.

(i x) FEATURE: oligonucleotide was synthesized by phosphoroamidite
method.
(D) OTHER INFORMATION: The sequence is listed from 3' to 5'
left to right and this is a part of SEQ ID NO:3.

(x i) SEQUENCE DESCRIPTION: SEQ ID NO:22:

CCGGAAGCAA 10

(2) INFORMATION FOR SEQ ID NO:23:

(i) SEQUENCE CHARACTERISTICS:
(A) LENGTH: 10 bases
(B) TYPE: nucleic acid
(C) STRANDEDNESS: single
(D) TOPOLOGY: Linear (i i) MOLECULE TYPE: chemically synthesized
desoxyribooligonucleotide.

(i x) FEATURE: oligonucleotide was synthesized by phosphoroamidite
method.
(D) OTHER INFORMATION: The sequence is listed from 3' to 5'
left to right and this is a part of SEQ ID NO:4.

(x i) SEQUENCE DESCRIPTION: SEQ ID NO:23:

CCGCCAGCAA 10

( 2 ) INFORMATION FOR SEQ ID NO:24:

( i ) SEQUENCE CHARACTERISTICS:
        ( A ) LENGTH: 8 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: letter M means the tethering to the
        support via oxidized 3-methyluridine.

( x i ) SEQUENCE DESCRIPTION: SEQ ID NO:24:

GGCCGTCG  8

( 2 ) INFORMATION FOR SEQ ID NO:25:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3'to 5'
        left to right and this is a part of SEQ ID NO:1.

( x i ) SEQUENCE DESCRIPTION: SEQ ID NO:25:

ACCGGCAGCA  10

( 2 ) INFORMATION FOR SEQ ID NO:26:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3'to 5'
        left to right and this is a part of SEQ ID NO:2.

( x i ) SEQUENCE DESCRIPTION: SEQ ID NO:26:

ACCGGTAGCA  10

( 2 ) INFORMATION FOR SEQ ID NO:27:

( i ) SEQUENCE CHARACTERISTICS:
        ( A ) LENGTH: 10 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide ( i x ) FEATURE: oligonucleotide was synthesized by phosphoroamidite
        method.
        ( D ) OTHER INFORMATION: The sequence is listed from 3'to 5'
        left to right and this is a part of SEQ ID NO:3.

( x i ) SEQUENCE DESCRIPTION: SEQ ID NO:27:

ACCGGAAGCA  10

( 2 ) INFORMATION FOR SEQ ID NO:28:

( i ) SEQUENCE CHARACTERISTICS:
    ( A ) LENGTH: 10 bases
    ( B ) TYPE: nucleic acid
    ( C ) STRANDEDNESS: single
    ( D ) TOPOLOGY: Linear ( i i ) MOLECULE TYPE: chemically synthesized
         desoxyribooligonucleotide.

( i x ) FEATURE: oligonucleotide was synthesized by phosphoroamidite
         method.
    ( D ) OTHER INFORMATION: The sequence is listed from 3' to 5'
         left to right and this is a part of SEQ ID NO:4.

( x i ) SEQUENCE DESCRIPTION: SEQ ID NO:28:

ACCGCCAGCA  10

( 2 ) INFORMATION FOR SEQ ID NO:29:

( i ) SEQUENCE CHARACTERISTICS:
    ( A ) LENGTH: 8 bases
    ( B ) TYPE: nucleic acid
    ( C ) STRANDEDNESS: single
    ( D ) TOPOLOGY: Linear ( i i ) MOLECULE TYPE: chemically synthesized
         desoxyribooligonucleotide.

( i x ) FEATURE: oligonucleotide was synthesized by phosphoroamidite
         method.
    ( D ) OTHER INFORMATION: letter M means the tethering to the
         support via oxidized 3-methyluridine.

( x i ) SEQUENCE DESCRIPTION: SEQ ID NO:29:

TGGCCGTC  8

( 2 ) INFORMATION FOR SEQ ID NO:30:

( i ) SEQUENCE CHARACTERISTICS:
    ( A ) LENGTH: 10 bases
    ( B ) TYPE: nucleic acid
    ( C ) STRANDEDNESS: single
    ( D ) TOPOLOGY: Linear ( i i ) MOLECULE TYPE: chemically synthesized
         desoxyribooligonucleotide.

( i x ) FEATURE: oligonucleotide was synthesized by phosphoroamidite
         method.
    ( D ) OTHER INFORMATION: The sequence is listed from 3' to 5'
         left to right and this is a part of SEQ ID NO:1.

( x i ) SEQUENCE DESCRIPTION: SEQ ID NO:30:

GACCGGCAGC  10

( 2 ) INFORMATION FOR SEQ ID NO:31:

( i ) SEQUENCE CHARACTERISTICS:
    ( A ) LENGTH: 10 bases
    ( B ) TYPE: nucleic acid
    ( C ) STRANDEDNESS: single
    ( D ) TOPOLOGY: Linear ( i i ) MOLECULE TYPE: chemically synthesized
         desoxyribooligonucleotide.

( i x ) FEATURE: oligonucleotide was synthesized by phosphoroamidite

-continued method.
(D) OTHER INFORMATION: The sequence is listed from 3'to 5'
left to right and this is a part of SEQ ID NO:2.

( x i ) SEQUENCE DESCRIPTION: SEQ ID NO:31:

GACCGGTAGC 10

( 2 ) INFORMATION FOR SEQ ID NO:32:

( i ) SEQUENCE CHARACTERISTICS:
(A) LENGTH: 10 bases
(B) TYPE: nucleic acid
(C) STRANDEDNESS: single
(D) TOPOLOGY: Linear ( i i ) MOLECULE TYPE: chemically synthesized
desoxyribooligonucleotide.

( i x ) FEATURE: oligonucleotide was synthesized by phosphoroamidite
method.
(D) OTHER INFORMATION: The sequence is listed from 3'to 5'
left to right and this is a part of SEQ ID NO:3.

( x i ) SEQUENCE DESCRIPTION: SEQ ID NO:32:

GACCGGAAGC 10

( 2 ) INFORMATION FOR SEQ ID NO:33:

( i ) SEQUENCE CHARACTERISTICS:
(A) LENGTH: 10 bases
(B) TYPE: nucleic acid
(C) STRANDEDNESS: single
(D) TOPOLOGY: Linear ( i i ) MOLECULE TYPE: chemically synthesized
desoxyribooligonucleotide.

( i x ) FEATURE: oligonucleotide was synthesized by phosphoroamidite
method.
(D) OTHER INFORMATION: The sequence is listed from 3'to 5'
left to right and this is a part of SEQ ID NO:4.

( x i ) SEQUENCE DESCRIPTION: SEQ ID NO:33:

GACCGCCAGC 10

( 2 ) INFORMATION FOR SEQ ID NO:34:

( i ) SEQUENCE CHARACTERISTICS:
(A) LENGTH: 8 bases
(B) TYPE: nucleic acid
(C) STRANDEDNESS: single
(D) TOPOLOGY: Linear ( i i ) MOLECULE TYPE: chemically synthesized
desoxyribooligonucleotide.

( i x ) FEATURE: oligonucleotide was synthesized by phosphoroamidite
method.
(D) OTHER INFORMATION: letter M means the tethering to the
support via oxidized 3-methyluridine.

( x i ) SEQUENCE DESCRIPTION: SEQ ID NO:34:

CTGGCCGT 8

( 2 ) INFORMATION FOR SEQ ID NO:35:

( i ) SEQUENCE CHARACTERISTICS:
(A) LENGTH: 10 bases
(B) TYPE: nucleic acid
(C) STRANDEDNESS: single
(D) TOPOLOGY: Linear ( i i ) MOLECULE TYPE: chemically synthesized
desoxyribooligonucleotide.

( i x ) FEATURE: oligonucleotide was synthesized by phosphoroamidite
method.
( D ) OTHER INFORMATION: The sequence is listed from 3' to 5'
left to right and this a part of SEQ ID NO:1.

( x i ) SEQUENCE DESCRIPTION: SEQ ID NO:35:

TGACCGGCAG 10

( 2 ) INFORMATION FOR SEQ ID NO:36:

( i ) SEQUENCE CHARACTERISTICS:
( A ) LENGTH: 10 bases
( B ) TYPE: nucleic acid
( C ) STRANDEDNESS: single
( D ) TOPOLOGY: Linear ( i i ) MOLECULE TYPE: chemically synthesized
desoxyribooligonucleotide.

( i x ) FEATURE: oligonucleotide was synthesized by phosphoroamidite
method.

( i x ) FEATURE:
( D ) OTHER INFORMATION: The sequence is listed from 3' to 5'
left to right and this is a part of SEQ ID NO:2.

( i ) SEQUENCE DESCRIPTION: SEQ ID NO:36:

TGACCGGTAG 10

( 2 ) INFORMATION FOR SEQ ID NO:37:

( i ) SEQUENCE CHARACTERISTICS:
( A ) LENGTH: 10 bases
( B ) TYPE: nucleic acid
( C ) STRANDEDNESS: single
( D ) TOPOLOGY: Linear ( i i ) MOLECULE TYPE: chemically synthesized
desoxyribooligonucleotide.

( i x ) FEATURE: oligonucleotide was synthesized by phosphoroamidite
method.
( D ) OTHER INFORMATION: The sequence is listed from 3' to 5'
left to right and this is a part of SEQ ID NO:3.

( x i ) SEQUENCE DESCRIPTION: SEQ ID NO:37:

TGACCGGAAG 10

( 2 ) INFORMATION FOR SEQ ID NO:38:

( i ) SEQUENCE CHARACTERISTICS:
( A ) LENGTH: 10 bases
( B ) TYPE: nucleic acid
( C ) STRANDEDNESS: single
( D ) TOPOLOGY: Linear ( i i ) MOLECULE TYPE: chemically synthesized
desoxyribooligonucleotide.

( i x ) FEATURE: oligonucleotide was synthesized by phosphoroamidite
method.
( D ) OTHER INFORMATION: The sequence is listed from 3' to 5'
left to right and this is a part of SEQ ID NO:4.

( x i ) SEQUENCE DESCRIPTION: SEQ ID NO:38:

TGACCGCCAG 10

( 2 ) INFORMATION FOR SEQ ID NO:39:

( i ) SEQUENCE CHARACTERISTICS:
    ( A ) LENGTH: 8 bases
    ( B ) TYPE: nucleic acid
    ( C ) STRANDEDNESS: single
    ( D ) TOPOLOGY: Linear ( i i ) MOLECULE TYPE: chemically synthesized desoxyribooligonucleotide.

( i x ) FEATURE: oligonucleotide was synthesized by phosphoroamidite method.
    ( D ) OTHER INFORMATION: letter M means the tethering to the support via oxidized 3-methyluridine.

( x i ) SEQUENCE DESCRIPTION: SEQ ID NO:39:

ACTGGCCG  8

( 2 ) INFORMATION FOR SEQ ID NO:40:

( i ) SEQUENCE CHARACTERISTICS:
    ( A ) LENGTH: 9 bases
    ( B ) TYPE: nucleic acid
    ( C ) STRANDEDNESS: single
    ( D ) TOPOLOGY: Linear ( i i ) MOLECULE TYPE: chemically synthesized desoxyribooligonucleotide.

( i x ) FEATURE: oligonucleotide was synthesized by phosphoroamidite method.
    ( D ) OTHER INFORMATION: The sequence is listed from 3' to 5' left to right and this is part of SEQ ID NO:1.

( x i ) SEQUENCE DESCRIPTION: SEQ ID NO:40:

TGACCGGCA  9

( 2 ) INFORMATION FOR SEQ ID NO:41:

( i ) SEQUENCE CHARACTERISTICS:
    ( A ) LENGTH: 9 bases
    ( B ) TYPE: nucleic acid
    ( C ) STRANDEDNESS: single
    ( D ) TOPOLOGY: Linear ( i i ) MOLECULE TYPE: chemically synthesized desoxyribooligonucleotide.

( i x ) FEATURE: oligonucleotide was synthesized by phosphoroamidite method.
    ( D ) OTHER INFORMATION: The sequence is listed from 3' to 5' left to right and this is a part of SEQ ID NO:2.

( x i ) SEQUENCE DESCRIPTION: SEQ ID NO:41:

TGACCGGTA  9

( 2 ) INFORMATION FOR SEQ ID NO:42:

( i ) SEQUENCE CHARACTERISTICS:
    ( A ) LENGTH: 9 bases
    ( B ) TYPE: nucleic acid
    ( C ) STRANDEDNESS: single
    ( D ) TOPOLOGY: Linear ( i i ) MOLECULE TYPE: chemically synthesized desoxyribooligonucleotide.

( i x ) FEATURE: oligonucleotide was synthesized by phosphoroamidite method.
    ( D ) OTHER INFORMATION: The sequence is listed from 3' to 5' left to right and this is a part of SEQ ID NO:3.

( x i ) SEQUENCE DESCRIPTION: SEQ ID NO:42:

TGACCGGAA  9

( 2 ) INFORMATION FOR SEQ ID NO:43:

( i ) SEQUENCE CHARACTERISTICS:
        ( A ) LENGTH: 9 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3' to 5'
        left to right and this is a part of SEQ ID NO:4.

( x i ) SEQUENCE DESCRIPTION: SEQ ID NO:43:

TGACCGCCA    9

( 2 ) INFORMATION FOR SEQ ID NO:44:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3' to 5'
        left to right and this is SEQ ID NO:1.

( x i ) SEQUENCE DESCRIPTION: SEQ ID NO:44:

TGACCGGCAG    CAAAATG    17

( 2 ) INFORMATION FOR SEQ ID NO:45:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3' to 5'
        left to right and this is SEQ ID NO:2.

( x i ) SEQUENCE DESCRIPTION: SEQ ID NO:45:

TGACCGGTAG    CAAAATG    17

( 2 ) INFORMATION FOR SEQ ID NO:46:

( i ) SEQUENCE CHARACTERISTICS:
        ( A ) LENGTH: 17 bases
        ( B ) TYPE: nucleic acid
        ( C ) STRANDEDNESS: single
        ( D ) TOPOLOGY: Linear ( i i ) MOLECULE TYPE: chemically synthesized
        desoxyribooligonucleotide.

( i x ) FEATURE: oligonucleotide was synthesized by phosphoroamidite
        method.
        ( D ) OTHER INFORMATION: The sequence is listed from 3' to 5'
        left to right and this is SEQ ID NO:3.

(x i) SEQUENCE DESCRIPTION: SEQ ID NO:46:

TGACCGGAAG CAAAATG 17

(2) INFORMATION FOR SEQ ID NO:47:

(i) SEQUENCE CHARACTERISTICS:
        (A) LENGTH: 17 bases
        (B) TYPE: nucleic acid
        (C) STRANDEDNESS: single
        (D) TOPOLOGY: Linear (i i) MOLECULE TYPE: chemically synthesized
        desoxyribooligonucleotide (i x) FEATURE: oligonucleotide was synthesized by phosphoroamidite
        method
        (D) OTHER INFORMATION: The sequence is listed from 3' to 5'
        left to right and this is SEQ ID NO:4.

(x i) SEQUENCE DESCRIPTION: SEQ ID NO:47:

TGACCGCCAG CAAAATG 17

METHODS OF DNA SEQUENCING BY HYBRIDIZATION BASED ON OPTIMIZING CONCENTRATION OF MATRIX-BOUND OLIGONUCLEOTIDE AND DEVICE FOR CARRYING OUT SAME

FIELD OF THE INVENTION

The present invention relates to molecular biology, and particularly to a method for determining DNA nucleotide sequences, and a device for carrying this out.

BACKGROUND OF THE INVENTION

By now, several methods have been described for assaying a nucleotide sequence and identifying individual substitutions of bases by hybridization techniques (Cotton, R. G. H. // Biochem. J, 1989, V. 263, pp. 1–10).

The most widespread techniques are those in which a test DNA fragment is attached to a membrane and hybridized thereon with labelled oligonucleotides (Wallace, P. B., Shaffer, J., Murphy, R. F., Bonner, J., Hirose, T., Itakura, K. //Nucleic Acid Res., 1979, V. 6 pp. 3543–3557).

Known in the art are a method and a device for determining a DNA nucleotide sequence (E. Southern et al., PCT/GB 89/00460, 1989), which method comprises synthesizing oligonucleotides on a glass support, effecting hybridization with radioactively- or fluorescently-labelled test DNA, washing in the duplex dissociation conditions, detecting the presence of individual substitutions in the test sequence by analyzing the autoradiographic patterns or the intensity of fluorescence at individual dots, and reconstructing the DNA nucleotide sequence on the basis of data analysis. A device for carrying out said method comprises a supporting film or glass plate and a matrix covalently attached to the surface thereof, the matrix comprising the whole set or a selected part of oligonucleotides of desired length, the latter oligonucleotides being capable of taking part in the hybridization reactions. The surface of the support to which the oligonucleotides are attached is made of glass.

The above method and device, however, have low sensitivity. The value of the signal from the labelled DNA (laid out in the near-surface layer of the support) obtained from each individual matrix element is limited by the substrate surface capacity (as regards the covalently attached oligonucleotides) and it cannot be raised without increasing either the area of the matrix element or the sensitivity of the labelling marker. These limitations reduce the resolving power of the method and device, make it difficult to miniaturize the matrix, increase the requirements imposed on the sensitivity and resolving power of the detector, and raise the consumption of the reagents. The method is rather complicated because, even in assaying a test DNA fragment, it requires a series of successive hybridizations to be performed, with additional rounds of oligonucleotide matrix synthesis to be performed at one-letter step, for each dot where hybridization has not yielded unambiguous information on the sequence and, therefore each time new optimal hybridization conditions (temperature, reagent concentrations, etc.) have to be chosen, which involves further experimentation and considerable expenditure of time and reagents.

DISCLOSURE OF THE INVENTION

It is an objective of the invention to alter the method and apparatus in such a way that to improve their efficiency, to increase sensitivity, accuracy and reproducibility, to simplify recognition of point mutations in the nucleotide sequence, and to reduce the expenditure of reagents.

In the present method for determining the DNA nucleotide sequence which comprises formation of an array of oligonucleotides, their hybridization with the labelled test DNA, washing under duplex dissociation conditions, identification of every single substitution of bases in the test DNA by analyzing distribution of the labelling marker, and eventual computerized reconstruction of the DNA nucleotide sequence, the above objective is achieved by that the invented method involves formation of an array of oligonucleotides at such concentrations thereof which ensure the desired temperature of duplex dissociation at the washing step.

To achieve reliable discrimination of fully complementary duplexes from duplexes having point mutations (mismatches), it is preferred to carry out the washing step at a fixed temperature gradient.

In order to improve accuracy and reduce the duration of data analysis it is preferred during washing to record the dependence of the amount of the remaining duplexes on the temperature to be compared with the dependence for the known sequence of perfect double helical DNA.

In order to simplify the technique and to reduce its duration, it is preferred to form an array of oligonucleotides at concentrations ensuring the same dissociation temperature for all fully complementary duplexes.

To reduce the duration of the analysis, it is advantageous to form an array of oligonucleotides at concentrations allowing the hybridization and washing of fully complementary duplexes to be carried out at the same temperature.

The present method makes it possible to considerably simplify the procedure as compared to the prior art method, and to improve its sensitivity, accuracy and reproducibility. The present method helps to improve the efficiency of the procedure by making it more economic in terms of time, labor, and reagents used. Furthermore, the size of the cells and the interstices between them are chosen in such a way as to conveniently combine the apparatus of the invention with the existing technological and measuring equipment.

The objective of the invention is further achieved by that the device for determining the DNA nucleotide sequence comprises a solid support and a matrix including an array of oligonucleotides of desired length, the matrix being attached, according to the invention, to the support by means of a gel layer having a thickness of no more than 30 μm. Preferably, the gel layer consists of a set of spaced "dots", according to the number of matrix elements. The gel layer provides for a three-dimensional attachment of the oligonucleotides at a capacity exceeding considerably the capacity of a molecular layer, while the gel layer comprising a plurality of spaced dots allows the desired number of oligonucleotides to be localized within a selected gel volume. All this makes it possible to miniaturize the matrix, and raise the rate of all the processes, and thus reduce the duration of the procedure, and improve the sensitivity, resolving power, accuracy and reproducibility of the method and device, and lower the consumption of the reagents.

A preferred embodiment of the present device is a device, in which the surface of each portion of the gel layer ("cell") has the shape of a square with a side length of 25 to 100 μm and the spacing between the squares equal to double the side length. This design permits a dynamic equilibrium to be rapidly established during the hybridization process, the consumption of reagents to be lowered, the sensitivity raised, and non-toxic, non-radioactive markers to be used.

In all the embodiments of the device, it is preferred to make the layer of a polyacrylamide gel which is convenient in use, readily available and reproducible.

The present device helps to simplify the procedure for determining a DNA nucleotide sequence, to reduce its duration, to improve the sensitivity, accuracy and reproducibility, and to lower the consumption of the reagents.

BRIEF DESCRIPTION OF THE DRAWINGS

The invention is explained below by a detailed description of its embodiments with reference to the accompanying drawings, as follows.

BEST MODE OF CARRYING OUT THE INVENTION

Figure 1:
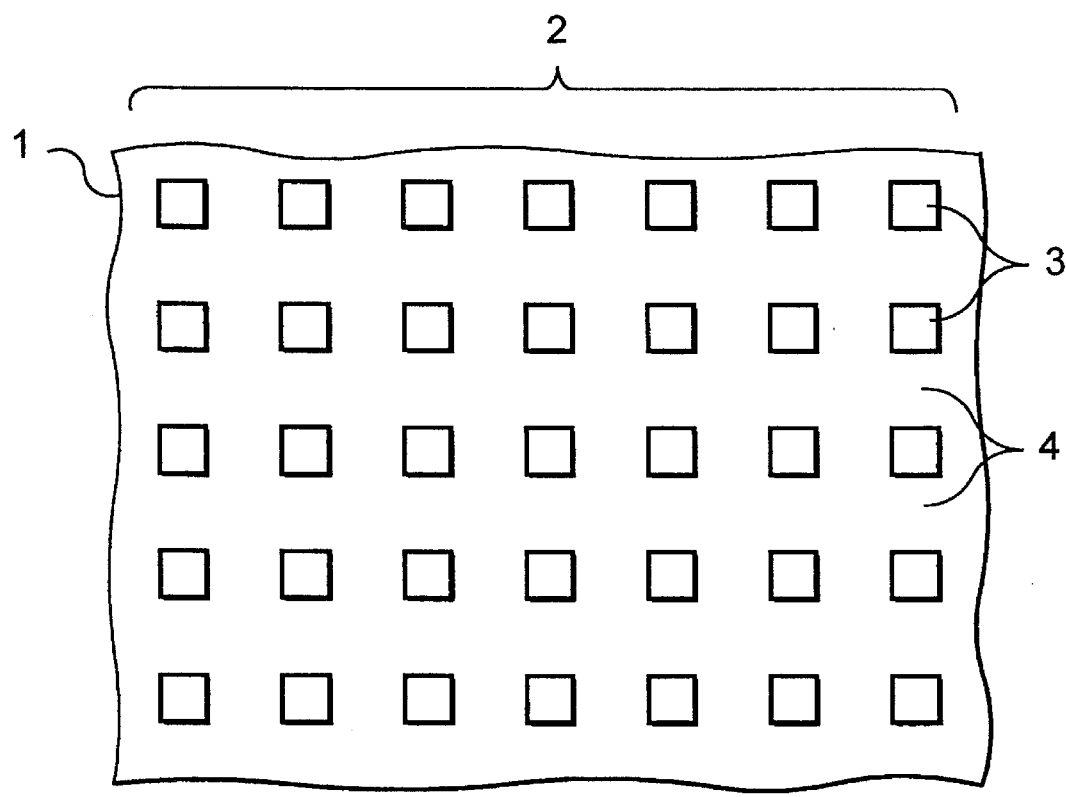
FIG. 1 is a scheme of the apparatus for determining the DNA nucleotide sequence as viewed from above.
Figure 2:
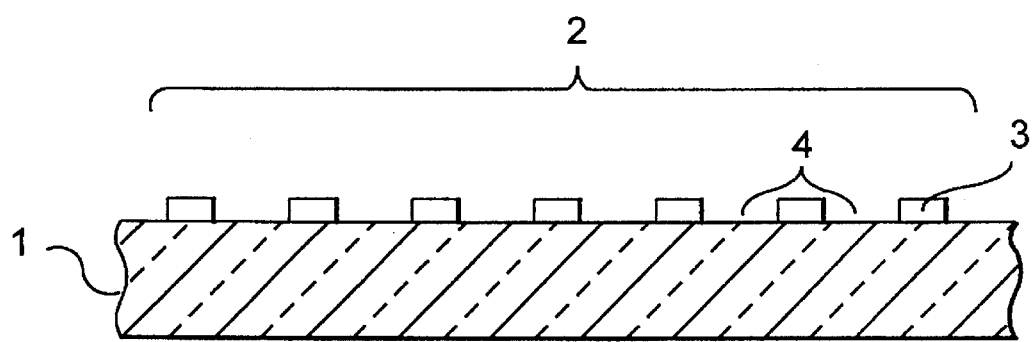
FIG. 2 is a longitudinal sectional view of FIG. 1.

The present device for determining DNA nucleotide sequence comprises support 1 (FIGS. 1 and 2), preferably a glass plate, and matrix 2 attached to the surface thereof by means of a gel layer of less than 30 μm thick. The gel layer may comprise a multitude of portions 3, according to the number of elements in matrix 2, spaced from one another by interstices 4. The interstices 4 may have different dimensions. The gel portions 3 may have different shapes.

A preferred device is one in which each portion 3 has the shape of a square with a side length of 25 to 100 μm and interstices 4 between the squares are equal to double the side length. The layer can be made of various gels, preferably a polyacrylamide gel.

The matrix can be manufactured as follows;

Two slides, one of which is pretreated with Bind Silane, and the other with Repel Silane, the latter slide was lubricated with a thin layer of Triton X-100. The slides are stacked with the use of spacers of less than 30 μm thick, the resulting spacing between them is filled with a gel solution and the gelling process is allowed to complete, whereupon the top slide is removed. The gel-coated lower slide is dried, part of the gel is removed, for example mechanically, so that the gel portions (cells) separated by interstices remain on the slide surface. The surface thus obtained is treated for 2 to 5 minutes with Repel Silane, washed first with alcohol and then with bidistilled water, and dried. Oligonucleotides containing 3-methyluridine at the 3'-end are oxidized with 1 mM of sodium periodate for 10 minutes to 1 hour at room temperature, precipitated with 10 volumes of 2% Li ClO$_4$ in acetone, and dissolved in water. Then, the oligonucleotides are immobilized in the gel. For this purpose, the cells of the air-dried matrix are filled with microdoses of oxidized oligonucleotides of identical volume (one type into one cell) from the available stock.

The array of the oligonucleotides is formed in such a way that their concentrations ensure the desired duplex dissociation temperature at the washing step. The array of oligonucleotides can be provided at concentrations ensuring the same dissociation temperature for all fully complementary duplexes or at concentrations allowing subsequent hybridizations and washing of fully complementary duplexes to be carried out at the same temperature. A test DNA fragment labelled with radioactive or fluorescent marker in a buffer solution is applied to the matrix with the preformed array of oligonucleotides (in the process, the solution fully covers all areas containing immobilized oligonucleotides). The array of oligonucleotides is then hybridized with the added labelled test DNA, and the duplexes are washed away in dissociation conditions. Single substitutions of bases in the test DNA are identified by analyzing distribution of the marker.

The test DNA sequence is reconstructed on the basis of data analysis. To reliably distinguish fully complementary duplexes with point mutations (mismatches), duplex washing in the present method is effected at a fixed temperature gradient. In order to reduce duration and improve accuracy of this analysis, it is preferred that in the course of washing the dependence of the amount of remaining duplexes on temperature should be determined and compared with the dependence for the known DNA sequence of perfect duplexes. It has been established that nearly always a temperature could be found at which the ratio of hybridization signals from a fully complementary duplex and a corresponding duplex containing point mutations is sufficiently high (at least 10:1) to reliably distinguish one from the other. The exception is provided by some terminal mismatches which may have a high stability. This does not, however, restrict the scope of the present method. Indeed, dealing with known sequences (for example, detecting mutations in them) it is always possible to select for immobilization such an oligonucleotide in which the expected base substitution would be located within the duplex. On the other hand, in analysis of an unknown nucleotide sequence (for example, in DNA sequencing), the problem of terminal mismatches can be easily solved by sacrificing some information while processing the data on hybridization between a DNA fragment and an oligonucleotide matrix by means of a computer. Our calculation methods are characterized by a high stability owing to excess information.

For a better understanding of the present invention, some aspects of its actual realization will be exemplified in the following.

EXAMPLE 1

Manufacture of a matrix with an array of oligonucleotides:

Oligonucleotides are synthesized by a solid-phase phosphoramidite method (protection is removed in a saturated aqueous ammonia solution at 55° C. for 12 hours) and purified by electrophoresis in a polyacrylamide gel. Oligonucleotides were labelled by ([γ-$^{32}$P]ATP by polynucleotide-kinase T4) at the 5'-end to achieve a specific activity of 3 μCi/pmole.

Two slides, one of which pretreated with Bind Silane and the other with Repel Silane (LKB) and lubricated with a thin layer of Triton X-100 are positioned at a distance from one another by means of 30 μm thick spacers. The resulting clearance between the slides is filled with 8% acrylamide solution, 30:1 N,N'-methylene bis-acrylamide, ammonium persulfate and TEMED, which is allowed to polymerize for 1 hour. As a result, a 30 μm thick gel layer is formed between the slides, the dimensions of the layer being determined by the size of the slides. When the polymerization is complete, the upper slide is removed. The lower slide coated with a polyacrylamide layer is treated with 50% hydrazine for 1 hour at room temperature.

Oligodesoxynucleotides containing 3-methyl uridine at the 3'-end are oxidized with 1 mM sodium periodate for 1 hour at room temperature, precipitated with 10 volumes of 2% LiClO$_4$ in acetone and dissolved in water. The air-dried matrix ready for immobilization is covered dropwise by means of a micromanipulator quipped with a capillary tip dispenser with 0.5 μl droplets of oxidized oligonucleotide (at a concentration of 10 pmol/μl). The plates are then exposed for 4 hours in a moist chamber, dried for 0.5 hour in open air, washed with a hybridization buffer (1M NaCl, 10 mM Na phosphate, pH 7.0, 1 mM ethylene diamine tetra-acetic acid), flushed with water and stored dry at −20° C. The oligonucleotides are immobilized in cells of a square matrix.

Figure 3:
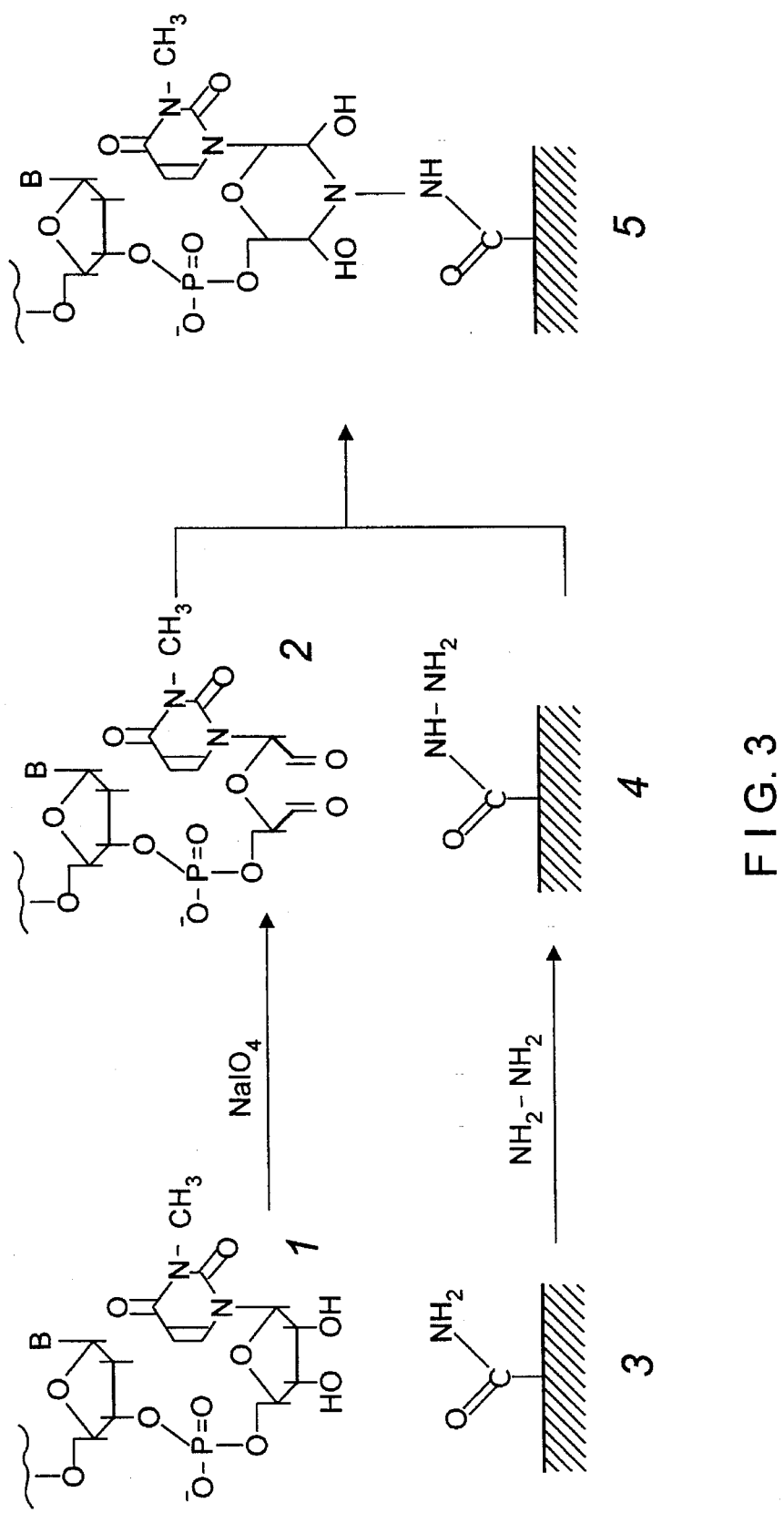
FIG. 3 is a scheme of chemical reactions occurring during immobilization of an oligonucleotide in a polyacrylamide gel.

The linker is represented by 3-methyluridine attached by a 5'-3' internucleotide phospho-diester bond to the oligonucleotide to be immobilized. 3-methyluridine was chosen due to the fact that it does not form strong hydrogen bonds with any natural bases. The scheme of the chemical reactions occurring in polyacrylamide gel during oligonucleotide immobilization is shown in FIG. 3.

The oxidation of the 3'-terminal ribonucleoside of oligonucleotide 1 (FIG. 3) with NaIO$_4$ produces a derivative 2 carrying a dialdehyde group at the 3'-end. On the other hand, when polyacrylamide 3 is treated with hydrazine, part of the amide groups are replaced with hydrazide groups 4, which readily react with 3'-dialdehyde, producing a relatively stable morpholine derivative 5.

The course of immobilization is monitored by the (5'-$^{32}$P] marker introduced by means of a kinase into the oligonucleotides to be immobilized. The yield of immobilization (that is, the proportion of oligonucleotides irreversibly bound to the gel) is 80%. At the same time, the yield for the unoxidized oligonucleotide used as a nonspecific sorption control does not exceed 2%. Therefore, the proportion of molecules bonded specifically through their 3'-end is 98%.

The bond between an oligonucleotide and polyacrylamide is stable enough for the matrix to withstand at least 5 to 7 hybridization/washing cycles without any noticeable change in its hybridizing properties. The half-life of the oligonucleotide-gel bond at 60° C. is 2 hours, and at 25° C., 36 hours.

The capacity of a carrier is evaluated by immobilizing the same amount of $^{32}$P-labeled oligonucleotide diluted by unlabeled oligonucleotide to various specific activities. 100 pmoles of a cold oligonucleotide per one dot (i.e., per 1 mm$^2$ of surface area or 0.03 mm$^3$ of gel volume) do not saturate the bonding. Similar experiments with an oxidized periodate α-$^{32}$P] UTP have shown that the gel capacity is equal to about 1 nmole per 1 mm$^2$ of the gel surface, which corresponds to the 30 mM concentration of active groups (concentration of amide groups is 1M in 8% polyacrylamide).

EXAMPLE 2

Reconstruction of the nucleotide sequence of a 17-membered desoxyoligonucleotide Hybridization of four heptadekanucleotides of the phage M13 sequence primer: 5'-d(GTAAAACGACGCCAGT) (SEQ ID NO: 1) and its three derivatives differing by one base (underlined):

5'-d(GTAAAACGATGGCCAGT) (SEQ ID NO: 2),

5'-d(GTAAAACGAAGGCCAGT) (SEQ ID NO: 3), and

5'-d(GTAAAACGACGGCCAGT) (SEQ ID NO: 4), with immobilized oligonucleotides (comprising 7, 8, 9, 12 or 15 monomer units) fully or partially complementary to different portions of heptadekamers is effected on an oligonucleotide matrix prepared as described in Example 1.

The labelled DNA fragment (0.01. μCi, 30 fmoles) in 1 μl of a hybridization buffer (1M NaCl, 10 mM of Na phosphate, pH 7.0, 1 mM ethylenediamine tetraacetic acid) is applied to a matrix of immobilized oligonucleotides so that each droplet of the hybridized mixture accurately covers the spot of the immobilized oligonucleotide, and incubated for 1 hour at 0° C. The matrix is flushed with the hybridization buffer at 0° C. and then washed 10 times, 1 minute each, with 20 ml of the same buffer at a temperature increased by 5° C. at each washing step. Upon each step, the hybridization signal is registered in each cell of the matrix through a lead collimator with a radioactivity counter (Minimonitor 125, Victoreen, USA) equipped with a pulse adder.

The ratio of residual radioactivity to the starting radioactivity at a given point is plotted on a logarithmic scale versus temperature (FIG. 4).

Figure 4A:
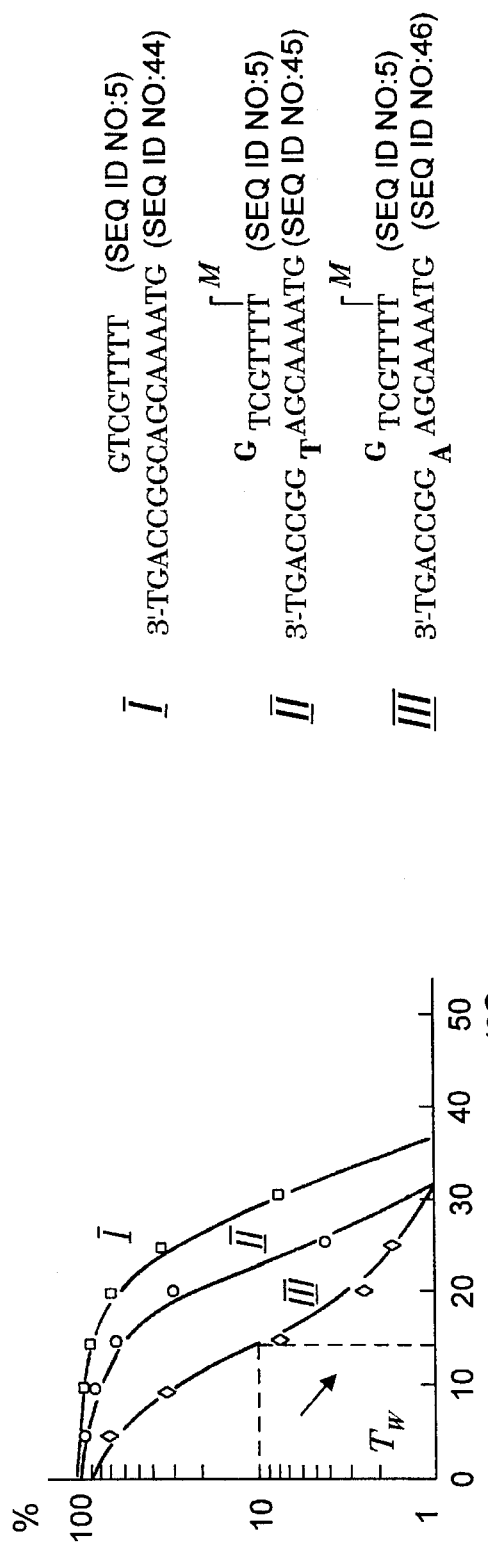
FIG. 4(a) shows the washing curves of AT-rich duplexes with the amount of the remaining duplexes plotted on the Y-axis, in %, and the washing temperature on the X-axis, in °C.
Figure 4B:
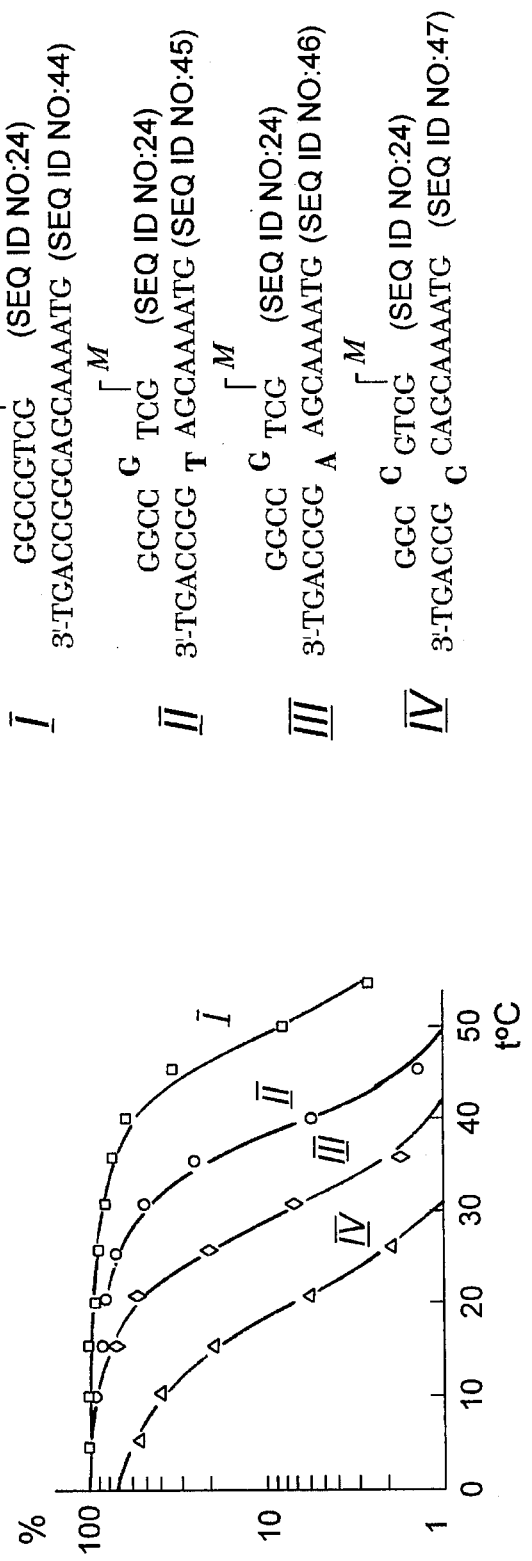
FIG. 4(b) shows the washing curves of GC-rich duplexes, with the amount of remaining duplexes plotted on the Y-axis, in %, and the washing temperature on the X-axis, in °C.

FIG. 4(a) and 4(b) show the washing curves of duplexes formed by the M13 primer or its analogous with AT-(FIG. 4a) and GC-rich (FIG. 4b) octanucleotides immobilized in gel, complementary to two different portions of the M13 primer, but producing defective duplexes with its derivatives (all the duplexes are shown in FIG. 4(a) and 4(b).

As the indicator of the duplex stability, the washing temperature (T$_w$) is chosen so that the hybridization signal at the corresponding point decreases by a factor of 10 compared with the starting level. The washing curves of the duplexes were determined for different volume concentrations of the immobilized oligonucleotide in gel. As is clear from FIG. 5, T$_w$ of a duplex depends strongly on the quantity of oligonucleotide immobilized in the spot of a given size. In the studied concentration range, the duplex washing temperature rises, within the experiment error, by a certain number of degrees when the immobilized oligonucleotide concentration becomes several times higher. This rule holds true for all the duplexes studied. In this way, the stability of each oligonucleotide can be varied. In this example, the concentration of 5 pmole per point keeps the duplexes stable within the range of 20° to 40° C.

In addition to the oligonucleotides shown in FIG. 4(a) and 4(b) large number of 7-, 8-, 9-, 12- and 15-membered substances, fully or partially complementary to the M13 primer, and duplexes containing other mismatch types, have been studied. The results of washing the duplexes of heptadekadesoxynucleotides with immobilized octadesoxynucleotides are shown in the Table.

As is clear from FIG. 4(a) and 4(b) and the Table, there is almost always a temperature at which the ratio of hybridization signals of a fully complementary duplex and a corresponding defective duplex is sufficiently high (at least 10) to reliably distinguish them. The exception is some terminal mismatches with abnormally high stability.

In the case of hybridization with octanucleotides, a sevenfold excess of information is obtained. Any nucleotide of a DNA fragment forms an inner pair with an immobilized oligonucleotide in six out of eight instances, whereas only in two instances it produces an end pair. A comparison is made between the washing curves to distinguish fully complementary duplexes from duplexes carrying point mutations and in this way single substitutions of bases in the DNA are detected. An initial heptadekamer is reconstructed from the overlapping of fully complementary duplexes.

EXAMPLE 3

The dependence of the duplex washing temperature on the concentration of an immobilized oligonucleotide can be determined as follows:

The procedure is similar to that of Example 1. The dependence of the duplex washing temperature $T_w$ on the concentration of an immobilized oligonucleotide is determined in a spot of 0.03 mm$^3$ volume within the oligonucleotide concentration range of 5.0, 1.5, 0.5 and 0.15 pmole.

Figure 5:
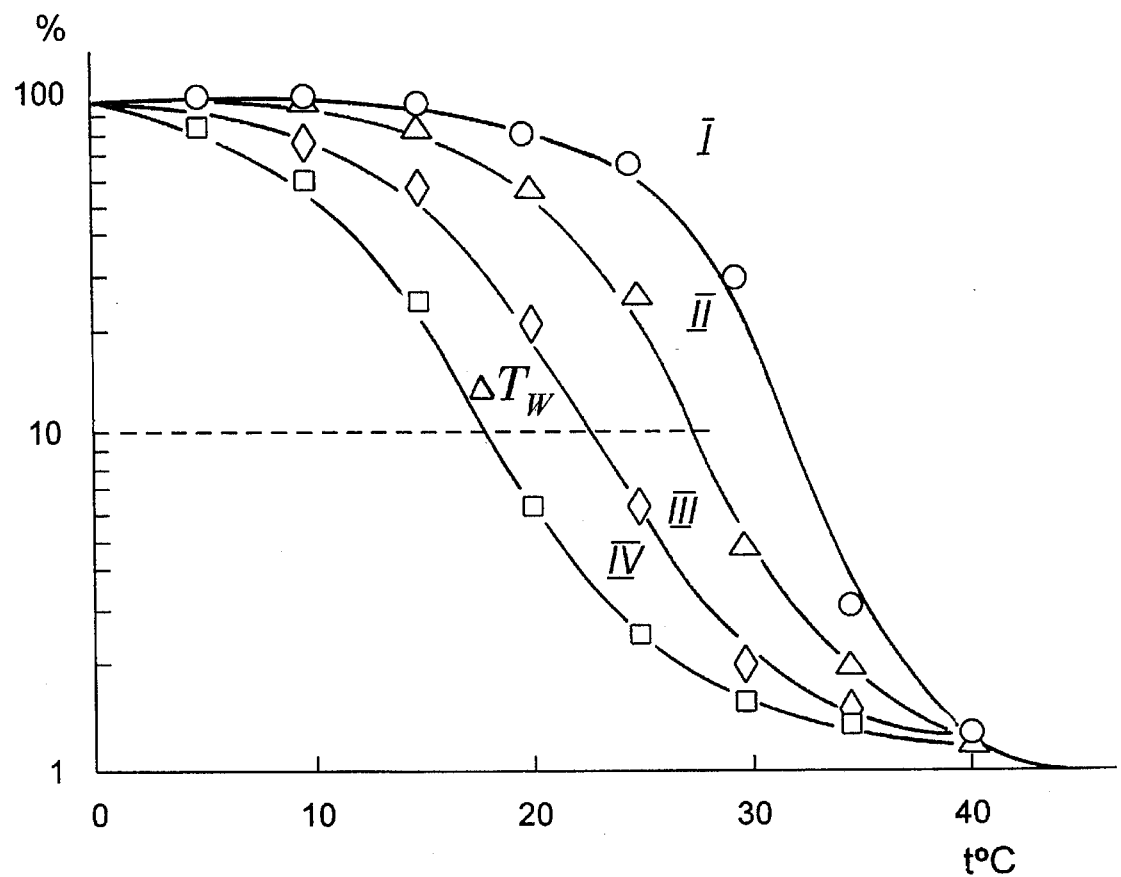
FIG. 5 presents the dependence of the duplex washing temperature (the duplex shown at top, M stands for matrix) on the concentration of immobilized oligonucleotide. The remaining duplexes are plotted on the Y-axis, in %, and the washing temperature on the X-axis, in °C.

The dependence of duplex washing curves on the volume concentration of an immobilized oligonucleotide in gel is shown in FIG. 5 (spot volume 0.03 mm$^3$ oligonucleotide concentration 5.0 (1), 1.5 (II), 0.5 (III) and 0.15 (IV) pmole). As is clear from the graph in FIG. 5, $T_w$ of a duplex depends heavily on the amount of oligonucleotides immobilized in a spot of given size. For the concentration range studied, the duplex washing temperature increases, within the experimental error, by a definite number of degrees while the concentration of immobilized oligonucleotide rises by a definite number of times. This rule holds for all the duplexes studied (FIG. 5 shows one example).

TABLE

Thermal Dissociation of Perfect Duplexes and Duplexes Containing Single Mismatches

| Perfect Duplexes ($T_w$, °C) | Mismatch GT ($\Delta T^*_w$, °C) | Mismatch GA ($\Delta T^*_w$, °C) | Mismatch CC ($\Delta T^*_w$, °C) |
|---|---|---|---|
| GTCGTTT(SEQ ID NO:5) / 3'-GCAGCAAAAT(SEQ ID NO:6) (28±0.5) | $G_T$TCGTTTT / 3'-$G_T$AGCAAAAT~ (−7±1) | $G_A$TCGTTTT / 3'-$G_A$AGCAAAAT (SEQ ID NO:8) (−16±2) | $C$GTCGTTT / 3'-$G_C$CAGCAAAA (SEQ ID NO:13) (−3±0.5) |
| CGTCGTTT(SEQ ID NO:9) / 3'-GGCAGCAAAA(SEQ ID NO:10) (28±0.5) | C$G_T$TCGTTT / 3'-GG$_T$AGCAAAA (SEQ ID NO:11) (−13±2) | C$G_A$TCGTTT / 3'-GG$_A$AGCAAAA (SEQ ID NO:12) (−21±1) | C$C$GTCGTT / 3'-G$C$CAGCAAA (SEQ ID NO:13) (−30±1) |
| CCGTCGTTT(SEQ ID NO:14) / 3'-CGGCAGCAAA(SEQ ID NO:15) (33±0.5) | CC$G_T$TCGTT / 3'-CG$G_T$AGCAA (SEQ ID NO:16) (−12±1) | CC$G_A$TCGTT / 3'-CG$G_A$AGCAA (SEQ ID NO:17) (−24±1) | C$C$GTCGTT / 3'-CG$_C$CAGCAA (SEQ ID NO:18) (−30±1) |
| GCCGTCGT(SEQ ID NO:19) / 3'-CCGGCAGCAA(SEQ ID NO:20) (41±0.5) | GCC$G_T$TCGT / 3'-CCG$G_T$AGCAA (SEQ ID NO:21) (−11±1.5) | GCC$G_A$TCGT / 3'-CCG$G_A$AGCAA (SEQ ID NO:22) (−25±1) | GC$C$GTCGT / 3'-CCG$_C$CAGCAA (SEQ ID NO:23) (−36±2) |
| GGCCGTCG(SEQ ID NO:24) / 3'-ACCGGCAGCA(SEQ ID NO:25) (50±0.5) | GGCC$G_T$TCG / 3'-ACCG$G_T$AGCA (SEQ ID NO:26) (−14±1.5) | GGCC$G_A$TCG / 3'-ACCG$G_A$AGCA (SEQ ID NO:27) (−23±1) | GGC$C$GTCG / 3'-ACCG$_C$CAGCA (SEQ ID NO:28) (−33±1) |
| TGGCCGTC(SEQ ID NO:29) / 3'-GACCGGCAGC(SEQ ID NO:30) (41±0.5) | TGGCC$G_T$TC / 3'-GACCG$G_T$AGC (SEQ ID NO:31) (−12±0.5) | TGGCC$G_A$TC / 3'-GACCG$G_A$AGC (SEQ ID NO:32) (−17±0.5) | TGGC$C$GTC / 3'-GACCG$_C$CAGC (SEQ ID NO:33) (−37±3) |
| CTGGCCGT(SEQ ID NO:34) / 3'-TGACCGGCAG(SEQ ID NO:35) (36±0.5) | CTGGCC$G_T$T / 3'-TGACCG$G_T$AG (SEQ ID NO:36) (−10±1.5) | CTGGCC$G_A$T / 3'-TGACCG$G_A$AG (SEQ ID NO:37) (−6±1) | CTGGC$C$GT / 3'-TGACCG$_C$CAG (SEQ ID NO:38) (−35±0.5) |

TABLE-continued

Thermal Dissociation of Perfect Duplexes and Duplexes Containing Single Mismatches

| Perfect Duplexes ($T_w$, °C.) | Mismatch GT ($\Delta T^*_w$, °C.) | Mismatch GA ($\Delta T^*_w$, °C.) | Mismatch CC ($\Delta T^*_w$, °C.) |
|---|---|---|---|
| ACTGGCCG⌐M<br>3'-TGACCGGCA(SEQ ID NO:40)~<br>(39 ± 1) | ACTGGCC⌐G<br>         G<br>3'-TGACCGG_TA(SEQ ID NO:41)~<br>         T<br>(-5 ± 1) | ACTGGCC⌐G<br>         G<br>3'-TGACCGG_AA(SEQ ID NO:42)~<br>         A<br>(-2 ± 0.5) | ACTGGC⌐C M<br>       C G<br>3'-TGACCG_C CA(SEQ ID NO:43)~<br>       C<br>(-30 ± 0.5) |

*Decrease in the washing temperature of a defective duplex compared with a perfect one
Note: Mismatches are given in bold type, M stands for matrix, and symbol "d" is omited for simplicity

EXAMPLE 4

The stability of fully complementary duplexes can be equalized as follows:

The procedure is the same as in Example 2, but the concentration varies for different immobilized oligonucleotides: 90 pmoles for AT, and 0.3 pmole for GC.

The dependence of stability (dissociation temperature) of duplexes on the concentration of immobilized oligonucleotides in gel makes it possible to detect mismatches in duplexes of different GC composition "on a single plate". In FIG. 4, the two shown immobilized oligonucleotides are very different in their GC content, and as a result the fully complementary duplex of the AT-rich oligonucleotide (FIG. 4a, curve I) is essentially less stable than the duplex of the GC-rich oligonucleotide containing mismatches (FIG. 4b, curves II and III). It must be clear that in this situation hybridization at a fixed temperature of a DNA fragment with a matrix containing both oligonucleotides will not allow to tell, within an accuracy of one base, whether or not this fragment has sequences complementary thereto.

Figure 6:
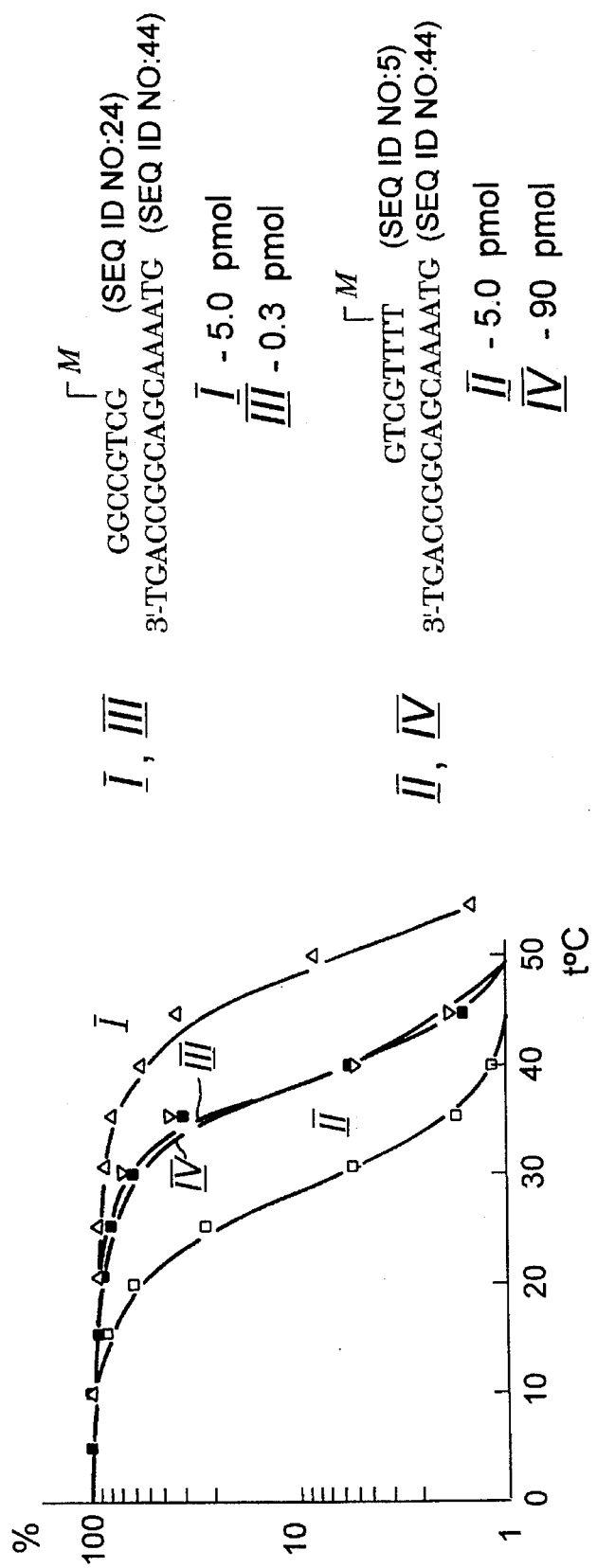
FIG. 6 shows the dependence of the washing temperatures of AT-rich and GC-rich duplexes on the concentration of oligonucleotides immobilized in gel. The amount of remaining duplexes, in %, are plotted on the Y-axis, and the washing temperature, in °C., on the X-axis.

The dependence of $T_w$ on the immobilized oligonucleotude concentration can be used to equalize dissociation temperatures of duplexes of different GC composition. As shown in FIG. 6, the washing curves of the AT- and GC-rich duplexes ($\Delta T_w=30°$ C. at the same concentration) can be brought into coincidence by properly selecting the concentrations of immobilized oligonucleotides at respective points.

One can equalize the washing curves of any array of oligonucleotides and thus obtain a "normalized" oligonucleotide matrix. The washing temperatures of fully complementary (perfect) duplexes for all the points of such a matrix are close to one another, therefore a single washing at an optimal temperature will suffice to unambiguously determine the points of the matrix where the DNA fragment under analysis has formed perfect duplexes.

EXAMPLE 5

The hybridization and washing steps can be performed at the same temperature on a "normalized" matrix containing preselected concentrations of immobilized oligonucleotides, as follows:

The procedure is carried out similarly to Example 4.

Figure 7:
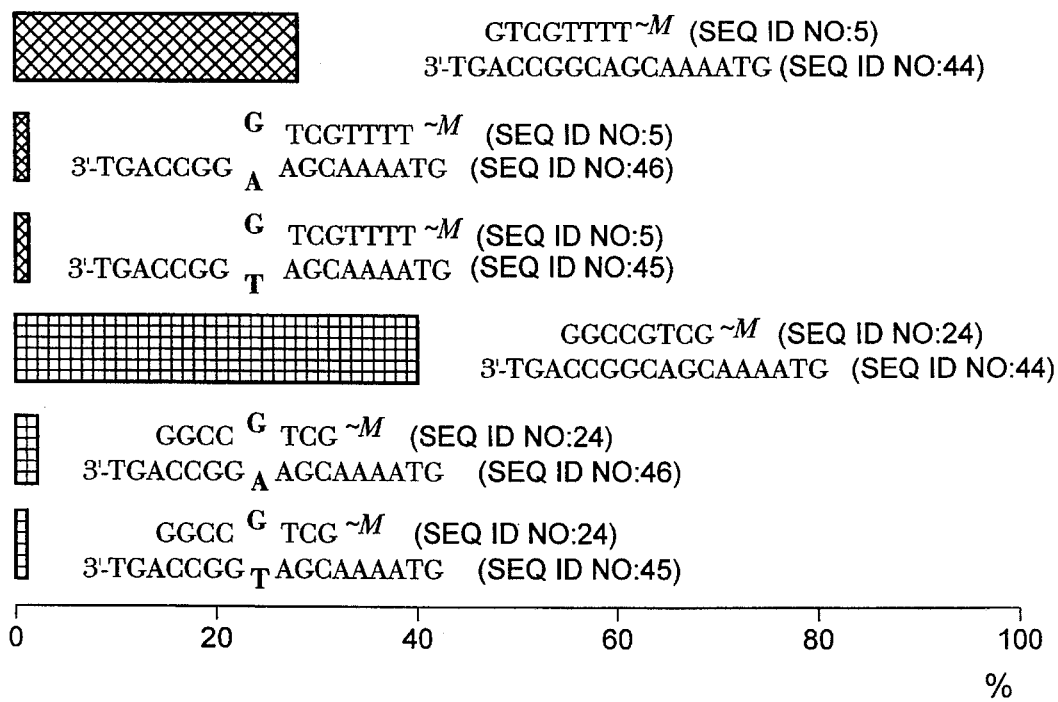
FIG. 7 is a comparative diagram for discriminating mismatches in duplexes of different GC composition on a matrix having selected concentrations of immobilized oligonucleotides.

The "normalized" matrix of two oligonucleotides (three points for each nucleotide) is hybridized and washed at 35° C. The principle can be understood from the comparative diagram in FIG. 7. Comparison of the residual signals indicates unambiguously the points where the duplexes were fully complementary, even though one terminal mismatch, GT, is very stable.

EXAMPLE 6

Sensitivity, accuracy and reproducibility of the present method and device are illustrated as follows:

An oligonucleotide matrix is prepared as described in Example 1, except that prior to treatment with 50% hydrazine the glass plate coated with a gel layer is air-dried and part of the gel is removed, for example mechanically, to form squares having the side of 25 to 100 µm spaced from one another by interstices of 50 to 200 µm, respectively.

Hybridization is carried out with fragments labelled at the 3' end by fluorescent tetramethylrhodamine marker, which is introduced with the help of a terminal polynucleotide transferase (comparison of the respective washing curves showed tetramethylrhodamine to exert no influence on the duplex stability).

Figure 8:
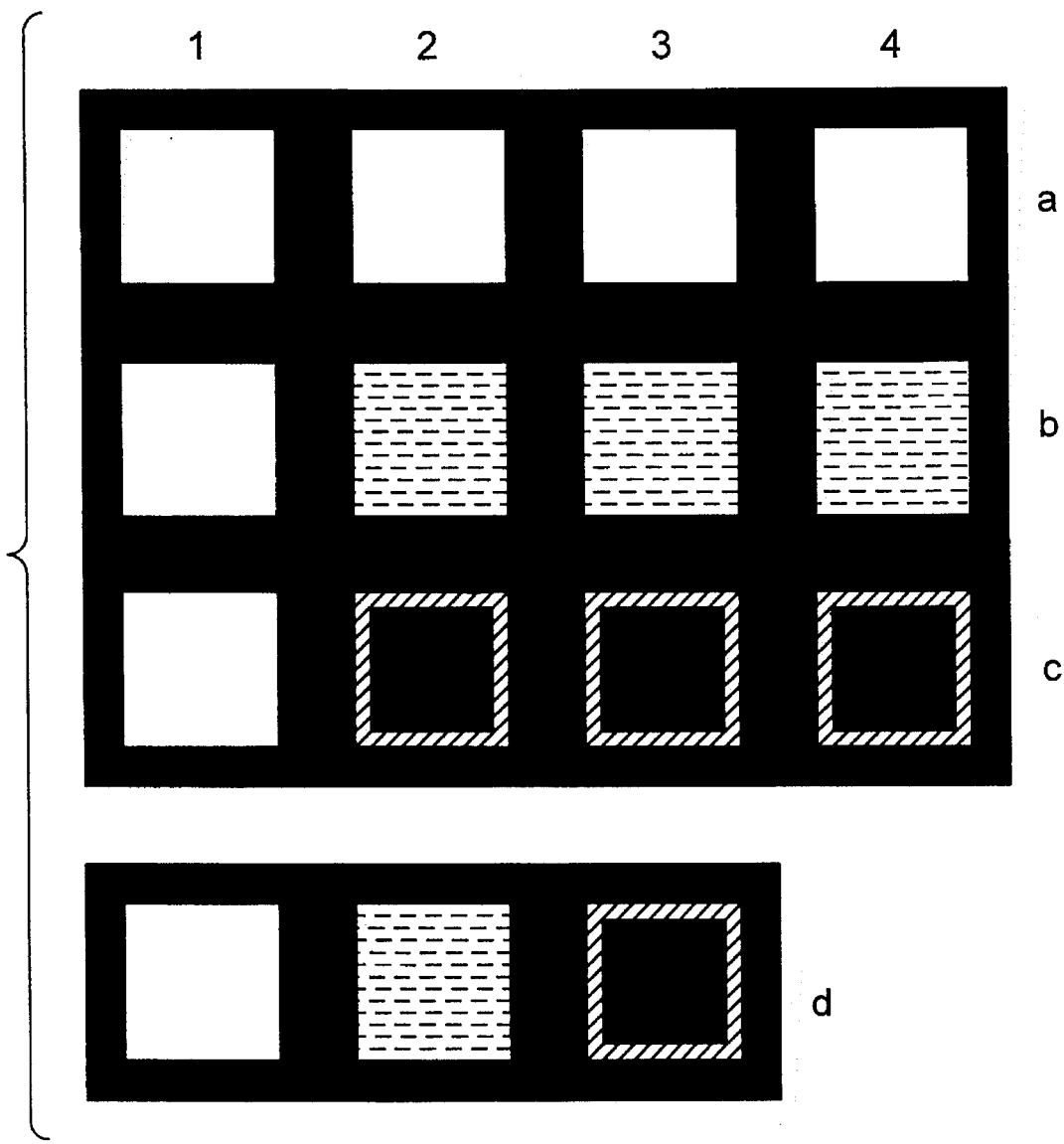
FIG. 8. The scheme of micro-matrix illustrates the specificity of hybridization and sensitivity of the method.

The use of a fluorescent marker allows hybridization to be carried out on a micro-scale. FIG. 8 shows a scheme of a micro-matrix, in which an octanucleotide 5'd(GGCCGTGG) is immobilized in gel squares having sides of 100 µm with 200 µm interstices between them. As can be seen in FIG. 8, a, hybridization with this matrix makes it possible to reliably detect substitutions of individual bases in the sequence (in FIG. 8), in square 1 (perfect duplex), and in squares 2, 3 and 4 (duplexes with mismatches GA, GT, and CC, respectively).

Similar experiments were carried out on micro-matrices, in which gel squares had the side of 25 µm, 30 µm, 50 µm, and 75 µm, with the interstices between them of 50 µm, 60 µm, 100 µm, and 140 µm, respectively.

Since distribution of the fluorescent marker can be measured at a very high sensitivity and spatial resolution (or example, with the aid of fluorescent microscope), detection of hybridization signals is limited only by the signal/background ratio and does not depend on the size of the object, whose fluorescence intensity is measured. Therefore, the sensitivity is inversely proportional to the area of the object(=oligonucleotide matrix cell). Miniaturization of the matrix allows the sensitivity of the method to be improved. For example, the squares "d" in FIG. 8, contain, respectively, 1 fmole, 100 amole and 10 amole of the tetramethylrhodamine derivative of desoxyuridine. The signal/background ratio for the square "d3" is equal to 2, which is sufficient to reliably assess the quantity of the substance.

INDUSTRIAL APPLICABILITY

The claimed method and device can be used in medicine, molecular biology, and agriculture for the purposes of genetic diagnostics, DNA sequencing and mapping, and mutation detection.

---

---

We claim:

1. A method for determining a DNA nucleotide sequence comprising:

a) providing a solid support with an attached matrix;

b) determining for each oligonucleotide member of a set of oligonucleotides to be bound to said matrix a concentration such that hybridization and washing of all fully complementary duplexes formed between said oligonucleotides and a labeled test DNA to be sequenced may be carried out at the same temperature, said concentration providing for the same dissociation temperature for all of said fully complementary duplexes;

c) forming an array of said oligonucleotides within said matrix, each oligonucleotide added at said determined concentration;

d) hybridizing said array of oligonucleotides with a labeled test DNA;

e) washing in conditions ensuring that imperfect duplexes are dissociated;

f) discriminating single-base substitutions in the test DNA by analyzing the distribution of the labeled test DNA; and g) determining the nucleotide sequence of the test DNA based on the results of the analysis in step f).

2. A method according to claim 1 wherein washing is carried out at a fixed temperature gradient.

3. A method according to claim 1 wherein dependence of an amount of remaining duplexes on temperature is determined during washing and compared with the dependence for a DNA of a known sequence.

4. A method for determining a DNA nucleotide sequence comprising:

a) providing a solid support with an attached matrix;

b) using an array of oligonucleotides wherein for each oligonucleotide member of the array to be bound to said matrix, a concentration has been determined such that hybridization and washing of all fully complementary duplexes formed between said oligonucleotides and a labeled test DNA to be sequenced may be carried out at the same temperature, said concentration providing for the same dissociation temperature for all of said fully complementary duplexes;

c) forming an array of said oligonucleotides within said matrix, each oligonucleotide added at said determined concentration;

d) hybridizing said array of oligonucleotides with a labeled test DNA;

e) washing in conditions ensuring that imperfect duplexes are dissociated;

f) discriminating single-base substitutions in the test DNA by analyzing the distribution of the labeled test DNA; and g) determining the nucleotide sequence of the test DNA based on the results of the analysis in step f).

5. A device for determining a nucleotide sequence, said device comprising:

(a) a solid support; and (b) a matrix affixed to said support, said matrix containing an array of oligonucleotides, the lengths and concentrations of the oligonucleotides being selected so that the nucleotide sequence can be determined after washing the matrix at a single temperature, said matrix formed by a multiplicity of gel portions according to the number of oligonucleotides in the array; wherein each gel portion contains one oligonucleotide of desired length and concentration from the array; said gel portions being separated from one another by interstitial spaces and the gel portions having a vertical height above the plane of the interstitial spaces of not more than 30 µm.

6. The device according to claim 5 wherein each of said gel portions have one surface attached to the solid support while the opposite surface is directed outward; said outward-directed surface being a square wherein a length of a side is from 25 to 100 µm and a width of said interstices is double the length of the side.

7. The device according to claim 5 wherein each of said gel portions contains an oligonucleotide of a single selected length.

8. A device for determining a nucleotide sequence said device comprising:

(a) a solid support; and (b) a matrix affixed to said support, said matrix containing an array of oligonucleotides of a single length and a concentration selected so that the nucleotide sequence can be determined after washing the matrix at a single temperature, said matrix formed by a multiplicity of gel portions according to the number of oligonucleotides in the array, wherein each gel portion contains one oligonucleotide of desired length and concentration from the array; said gel portions being separated from one another by interstitial spaces and the gel portions having a vertical height above the plane of interstitial spaces of not more than 30 μm.

9. A method for determining the sequence of a test nucleotide molecule:

(a) providing an array of oligonucleotides wherein the array are present at concentrations effective to distinguish a perfect duplex from a one-base mismatch at a given temperature;

(b) hybridizing the test nucleotide molecule to the oligonucleotides in the array;

(c) washing the array at the given temperature; and (d) determining the oligonucleotides in the array which hybridized to the test nucleotide molecule to obtain information about the sequence of the test nucleotide molecule.

* * * * *